(12) United States Patent
Epley et al.

(10) Patent No.: US 7,559,766 B2
(45) Date of Patent: Jul. 14, 2009

(54) HEMISPHEROIDAL-TRUSS SPATIAL MANIPULATOR SYSTEM AND APPARATUS

(75) Inventors: John Epley, Portland, OR (US); William J. McDonough, Portland, OR (US)

(73) Assignee: Epley Research, LLC, Portland, OR (US)

(*) Notice: Subject to any disclaimer, the term of this patent is extended or adjusted under 35 U.S.C. 154(b) by 691 days.

(21) Appl. No.: 11/289,201

(22) Filed: Nov. 28, 2005

(65) Prior Publication Data

US 2007/0167886 A1 Jul. 19, 2007

Related U.S. Application Data

(60) Provisional application No. 60/631,336, filed on Nov. 29, 2004.

(51) Int. Cl.
*G09B 19/16* (2006.01)
(52) U.S. Cl. .......................................................... 434/34
(58) Field of Classification Search ............ 434/29, 434/30, 34, 55–58, 17, 47, 78
See application file for complete search history.

(56) References Cited

U.S. PATENT DOCUMENTS

| | | | | |
|---|---|---|---|---|
| 3,083,037 A | * | 3/1963 | Gordon et al. | 280/206 |
| 3,141,669 A | * | 7/1964 | Chul | 472/17 |
| 3,164,382 A | * | 1/1965 | Johnson | 472/17 |
| 3,936,047 A | * | 2/1976 | Brandt et al. | 482/146 |
| 4,402,500 A | * | 9/1983 | Coles | 472/17 |
| 4,799,667 A | * | 1/1989 | Suchy | 472/17 |
| 4,824,099 A | * | 4/1989 | Rusu et al. | 472/3 |
| 5,759,107 A | * | 6/1998 | Nagel | 472/47 |

(Continued)

FOREIGN PATENT DOCUMENTS

WO WO/04/000191 12/2003

(Continued)

OTHER PUBLICATIONS

International Preliminary Report on Patentability for International Patent application No. PCT/US06/45496; IPEA/US; Aug. 19, 2008; 5 pages.

*Primary Examiner*—Kurt Fernstrom
(74) *Attorney, Agent, or Firm*—Ater Wynne LLP

(57) ABSTRACT

Spatial manipulator apparatus for a mammalian subject includes a stabilizing base; a hemispheroidal truss frame mounted for rotation on the stabilizing base, the truss frame supporting and stabilizing an outer generally circular rim in relation to a non-concentric hub located at its rotational axis; and a second frame mounted orthogonally within the outer rim on a second rotational axis, the second frame being configured to support a mammalian subject during spatial manipulation thereof by rotation about one or more of the orthogonal rotational axes. Preferably, the truss frame and the second frame are driven for rotation about the orthogonal rotational axes to achieve a desired mammalian-subject spatial orientation within a chair-like structure pivotally adjustably mounted within the second frame. Preferably, the truss frame includes a substantially circular rim member mounting the second frame for rotation therein; three or more struts connecting from circumferential substantially evenly spaced locations along the circular rim member to a point of convergence on the truss frame through which the first axis extends; and a hub at the point of convergence mounting the three or more struts.

33 Claims, 6 Drawing Sheets

U.S. PATENT DOCUMENTS

| | | | | |
|---|---|---|---|---|
| 5,792,031 A | * | 8/1998 | Alton | 482/78 |
| 5,980,256 A | * | 11/1999 | Carmein | 434/55 |
| 6,017,276 A | * | 1/2000 | Elson et al. | 472/60 |
| 6,355,048 B1 | * | 3/2002 | Hong et al. | 606/130 |
| 6,500,097 B1 | * | 12/2002 | Hall | 482/54 |
| 7,119,471 B2 | | 10/2006 | Kiderman et al. | |

FOREIGN PATENT DOCUMENTS

WO　　WO/2005/048907　　6/2005

* cited by examiner

HEMISPHEROIDAL-TRUSS SPATIAL MANIPULATOR SYSTEM AND APPARATUS

RELATED APPLICATIONS

The present application claims priority to U.S. Provisional Patent Application Ser. No. 60/631,336, entitled HEMISPHERE-TRUSS SPATIAL MANIPULATOR and filed Nov. 29, 2004, the disclosure of which is incorporated herein in its entirety by this reference.

BACKGROUND OF THE INVENTION

This invention relates generally to the field of spatial manipulators for orienting human subjects in 3-dimensional (3D) space. More particularly, it concerns a spatial manipulator for a) maneuvering a mammalian subject's (e.g. a human or other biped's) vestibular apparatus in relationship to gravity for purposes of diagnosis and treatment of certain vestibular disorders, as well as positioning a subject to undergo other medical diagnostic or therapeutic procedures, b) simulating inner or outer space flight or other external environmental perturbations (e.g. aeronautic, vehicular or vessel travel) such as turbulence or oscillation and c) entertainment or education, e.g. driver/pilot training or gaming.

Dizziness and positional vertigo, serious conditions affecting the lives of many people, are typically sourced to the root cause of vestibular malfunction and other chronic vertiginous conditions. Much experience in the past with examining and treating a person with vestibular-disorder has focused, and correctly so, on "misplaced" anatomical particles, called "otoliths", present in the person's semi-circular canal systems. These wandering otoliths, have broken loose from their original location attached to the otolithic organ to which they have provided gravity sensitivity by virtue of their high density and have migrated to the semicircular canals wherein they have create a false sense of rotational movement and dizziness Effective treatment, in many instances, has been determined to involve putting such a person, and specifically the persons' head, through various three-dimensional spatial-orientation maneuvers, both to allow a doctor/clinician better to identify the specific nature of an apparent vestibular disorder, and also to employ such maneuvering, assisted by gravity, to "reposition" the displaced otoliths out of the semicircular canals so that they will no longer create their adverse affects.

Audiology and cardiology and other diagnostic testing and treatment also sometimes require putting a patient's body through such three-dimensional spatial-orientational maneuvers, e.g. to test a subject's hearing or balance or heart or blood pressure in response to orientational positions or changes, rotational speeds or accelerations, vibratory stimulus and the like.

There is also need fore apparatus capable of simply and conveniently providing an environment for simulation of inner or outer space flight, vehicular or vessel travel, including with turbulence or oscillation, the apparatus requiring a minimum of space, weight and expense. Such applications include education, e.g. flight or driver's training and entertainment, e.g. games such as fighter pilot or NASCAR driver, skydiver, Motocross, skateboarding, snowboarding, skiing or other extreme sports, etc.

Mammalian subjects as used herein refers broadly to mammals, and preferably bipeds and most preferably humans that are capable of diagnosis and therapy (treatment) for vestibular disorders or are candidates for flight simulation or other applications requiring many degrees of freedom of rotational orientation. Such orientations of the mammalian subject preferably would have permitted concurrent proximate access to the mammalian subject for purposes of monitoring the mammalian subject's vestibular or other physiological response to such rotation or vibration.

Unfortunately, certain forms of prior art apparatus typically are spherical, i.e. they describe a circle no matter the viewing angle. As such, this form of prior art apparatus typically provides only limited access to a subject positioned within the sphere. Moreover, certain forms of prior art apparatus typically are passive, rather than driven, so that there is little or no control of the orientation of the subject, and, at best, only manual control. This prior art shortcoming is understandable, since most prior art apparatus are intended to be used for recreation rather than for serious scientific, e.g. medical testing or treatment, applications.

Among conventional medical treatment apparatus, a rotatable chair has been provided that can be tilted backward, off-vertical-axis, while rotating a patient. Too few degrees of rotational freedom are provided by such apparatus, as there is no orthogonal-axes 360° rotational orientation of the patient. Moreover, the tilt angle range is somewhat limited. Barrel-like apparatus with more degrees of freedom and range also have been provided, but these deny real-time attendant, e.g. physician or technician access due to the cylindrical-surround shape of the barrels. Other forms are unbalanced, requiring the motors to work against gravity. Others are infeasibly bulky.

One recent development involves apparatus having a single boom assembly that is asymmetrically attached to one side of a circular rim for providing a relatively stationary bearing at the rim's rotational axis. This boom assembly involved the use of struts that are attached asymmetrically at one circumferential region of the rim, providing little or no structural integrity to the rim itself, which buckles and deforms under the weight of a second-axis frame assembly mounted therein and mounting a chair on which a subject sits. The rim was of triangular cross section rendered in solid steel and was supported by a solid steel circumferential ring of rectangular cross section. This configuration required a four-roller circumferential race to maintain even a low-level of structural integrity when the rim and/or the frame assembly was rotated under slight or even no load. With this recently developed apparatus, maintaining the structural integrity of the circular and planar and earth-vertical planar orientation of the rim was extremely problematic and operational failures characterized by rim buckling and other deformation and ultimate malfunction were commonplace.

SUMMARY OF THE INVENTION

The invented spatial manipulator apparatus for a mammalian subject includes a stabilizing base; a hemispheroidal truss frame mounted for rotation on the stabilizing base, the truss frame supporting and stabilizing an outer generally circular rim in relation to a non-concentric hub located at its rotational axis; and a second frame mounted orthogonally within the outer rim on a second rotational axis, the second frame being configured to support a mammalian subject during spatial manipulation thereof by active (e.g. motor driven) rotation about one or more of the orthogonal rotational axes. Preferably, the truss frame and the second frame are driven for rotation about the orthogonal rotational axes to achieve a desired mammalian-subject spatial orientation within a chair-like structure pivotally adjustably mounted within the second frame. Preferably, the truss frame includes a substantially circular rim member mounting the second frame for rotation therein; three or more struts connecting from circumferential substantially evenly spaced locations along the circular rim member to a point of convergence on the truss frame through which the first axis extends; and a hub at the point of convergence mounting the three or more struts.

DETAILED DESCRIPTION OF THE PREFERRED EMBODIMENTS

Figure 1:
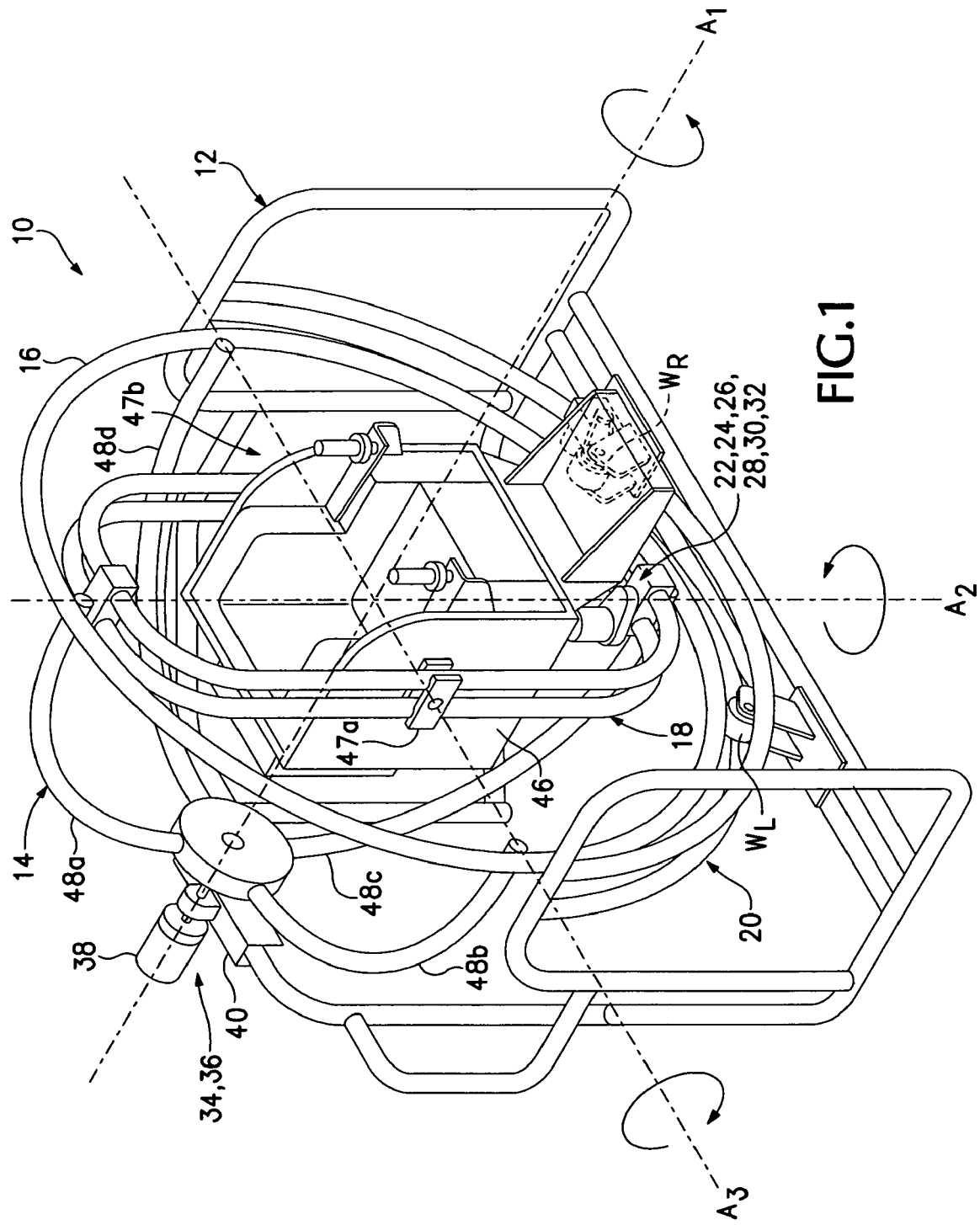
FIG. 1 is a front isometric view of the apparatus, in accordance with one embodiment of the invention, including a base, a hemispheroidal truss frame mounted for rotation in the base and a second frame or subject support mechanism mounted for orthogonal rotation within the hemispheric truss.

The present invention provides for diagnosis and treatment of vestibular and other medical disorders, for flight or driver simulation and training, for entertainment and gaming or for other spatial manipulation applications the required degrees of freedom, e.g. three-dimensional (3D) 360° rotation or 360° rotation about at least two orthogonal axes that allows achievement of any desired one or more of an infinite number of 3D spatial orientations and optional concurrent vibrations, e.g. oscillations, in a lightweight apparatus that has the needed structural integrity and reliability that has eluded conventional design approaches.

In this setting, the present invention offers a unique, very lightweight but sturdy, relatively inexpensive, low space-occupying and rotationally versatile, spatial manipulator with high structural integrity. This manipulator, two different versions of which are illustrated in the accompanying drawings, provides a significant improvement over prior-art, somewhat similar, manipulator structures which are heavy, bulky and expensive. The hemispheroidal truss structure supporting the first axis circular rim provides structural integrity to the rim in both its circular and planar aspects necessary for smooth and safe operation of the entire apparatus, and thereby provides a significant advantage over the prior art.

Those of skill in the art will appreciate that the rotatable truss spatial manipulator described and illustrated herein is substantially hemispherical, i.e. it is as close as practical given manufacturing tolerances to defining the shape of a true hemisphere. Nevertheless, slightly oblate or piece-wise curvilinear or angled or otherwise out-of-round shapes that approximate that of a true hemisphere are within the scope of the invention, since they can alternatively function as described herein. Thus, the intentionally broad term "hemispheroidal" is used herein to describe as broadly as possible the approximately hemispherical shape of the truss frame.

As just mentioned, accompanying this narrative are several detailed and component-labeled drawings fully illustrating two preferred and best mode embodiments of the proposed manipulator of this invention. This manipulator, formed, as can be seen, principally with small, lightweight, hollow tubular elements, features a unique, hollow, hemispherical motion-truss-frame which is quite "spidery" in nature. In one of the embodiments illustrated herein, most of the truss frame members including the struts are smoothly curved along their lengths. In the other illustrated embodiment, many of these truss frame members including the struts are piece-wise linear and angled relative to one another to describe a curve, with the resulting truss frame taking on a configuration similar to a geodesic dome.

Identified, plural rotational axes (e.g. two in number) are furnished, and motion about these axes is preferably, though not necessarily, introduced through precision-computer-operated rotary and linear motors. Rotary motion of the main hemispherical truss frame is supported through a pair of arcuately spaced idler/drive rollers supported between a spaced pair of semi-circular outer rails that form a rim-support brace member. Another, e.g. a third, rotational axis orthogonal to both of the first two rotational axes is furnished around which a subject-support chair can be pivoted properly to align the subject's semicircular ear canals relative to the vertical plane defined by the circular rim.

The main truss frame is supported for rotation of the rim in a generally upright plane about a first, horizontal axis. A sub-frame or second, preferably oval, frame is carried on and generally within the truss frame rim, and is supported for rotation about a second axis which is orthogonal to the first axis, the second axis residing in the plane of rotation of the truss frame that is normal to the first axis. A subject-support structure generally in the form of a chair is mounted on the sub-frame for rotation about the second axis, the subject-support structure defining a third axis that is orthogonal to the first and second axes that provides for at least pivotal (typically less than 360°) rotational orientation and at least temporary fixation of the chair structure relative to the second axis frame in the pitch plane of the subject in order to properly align an individual subject's particular anatomy, e.g. an inner ear canal, relative to the earth or horizontal reference plane.

In operation, this third axis can be adjusted in the pitch plane of the subject that has been placed and held fixedly within the chair structure, so that the general plane of the horizontal semicircular canals within the subject's head bears a fixed relationship to the plane of rotation of the second axis, and thus any rotation of the second axis structure on its axis provides motion that is co-planar with the general plane of the subject's horizontal semicircular canals. This adjustability feature further provides a means of calibration of the head in its pitch plane so that any accompanying software can operate to generally display and maneuver in relationship to the orientation of the subject's individual semicircular canals. This adjustment of the subject's relationship to the second axis by selectively pivoting and then fixing the third axis in relationship to certain known anatomical landmarks that generally orient that relationship to the subject's semicircular canals provides another advantage over the prior art.

All principal features of the invention are illustrated in the accompanying drawings.

Characterization of the Invention

1. One way to describe the invention is to see it as being a plural-axis motion manipulator for placing a human subject selectively in different spatial orientations, or moving the subject selectively through different spatial planes, as may be required for either diagnostic or therapeutic (treatment) maneuvers of the subject. The manipulator includes: (a) a generally hemispheroidal motion truss frame supported for rotation about a first, generally horizontal axis; (b) a sub-frame mounted on the truss frame for rotation about an axis which is orthogonal with respect to the axis of rotation of the truss frame; and (c), a subject support structure (preferably somewhat chair-like) mounted on the sub-frame for rotation about another third axis which is orthogonal with respect to the first- and second-mentioned axis. Those of skill in the art will understand that the third axis that is perpendicular to the second axis passes from the second axis frame through the chair from side to side and provides an adjustment of the chair in what will be referred to herein as the "pitch plane" of the subject.

2. Another view of the invention is one which includes the description stated in Characterization 1, wherein the truss frame possesses a generally flat, upright, open side defined, at least in part, by a substantially circular frame rim, and where the truss frame is supported for rotation through idler rollers carried on a circular track provided in a static frame, with the truss frame rim, the circular track, and the mentioned idler rollers cooperating much in the fashion of the inner and outer races in a ring-like roller-bearing structure.

3. A further characterization includes the description of Characterization 1, wherein the truss frame possesses a generally open hemispheroidal side, and selectively mountable on that hemispheroidal side is a thin, hollow, hemispheroidal surface shell, whether assembled from component parts or unitary and integral in structure, which shell allows for visual occluding of the hemispheroidal side of the truss frame.

FIG. 1 illustrates the apparatus in an isometric view at 10. Apparatus 10 includes a base 12, a hemispheroidal truss frame or shell 14 having a circular rim 16, the frame or shell being rotatable about a first substantially horizontal axis $A_1$ and a second, preferably oval, frame 18 generally centered within rim 16 and rotatable about a second axis $A_2$ that is substantially orthogonal to first axis $A_1$. Those of skill in the art will appreciate that, generally speaking, truss frame 14 is rotatable through 360° and second frame 18 is rotatable within truss frame 14 also through 360°. This renders apparatus 10 capable of substantially full, controlled rotational freedom to orient a mammalian, e.g. human, subject, supported within second frame 18 in a desired orientation relative to the earth or other reference plane.

Hemispheroidal truss frame 14 is remarkable in its overall shape, in view of the generally spherical prior art apparatus, because it is hemispherical, i.e. it provides a broad circular planar opening in a vertical plane containing second rotational axis $A_2$ that permits free access to the mammalian subject for treatment or setup purposes. Prior art apparatus have depended for the most part on the circular symmetry of a spherical cage when viewed from any angle, whereas the invented apparatus 10 is asymmetric in overall shape when viewed from the side elevation. This overall shape provides not only easy access in the region of the circular planar opening, but also provides a smaller footprint that may be seen by brief reference to FIG. 2 as saving floor space when situated in the corner of a room. One of ordinary skill in the art would assume that such asymmetry in overall shape would render apparatus 10 unstable or incapable of controlled, safe, secure rotation under the approximately 100-300 pound burden of a rotating human subject. But as will be seen, the structure of apparatus 10 uniquely positions it as a low-cost, lightweight, durable, stable, space-saving alternative to prior art devices.

Moreover, it may be seen from FIG. 1 that truss frame 14 is mounted for rotation on base 12 by an upwardly extending semi-circular rim-support brace member 20 that cradles and stabilizes rim 16 of truss frame 14. Remarkably, again, full circumferential support structure is not required for static and dynamic structural stability under rotational stress and torsional forces. Indeed, rim-support brace member 20 reaches a height that is less than or equal to approximately half the height of truss frame 14. Nevertheless, truss frame 14 rotating above base 12 with subject-loaded second frame 18 rotating therein is structurally stable and resists both base creep and rim derailment. Importantly, it does so without resort to external circumferential races or capture or containing members or mechanisms. This is by virtue of structural details to be described further below.

In accordance with a preferred embodiment of the invention, those of skill in the art will appreciate that the center of mass of second frame 18 with a subject properly situated therein is congruent with the intersection of first and second axes $A_1$ and $A_2$. This provides the advantage of symmetrical loading during rotation of the subject and minimal off-axis linear speed or acceleration relative to either of the two orthogonal rotational axes. As a result, operation of apparatus 10 is much more stable and smooth over a broad range of angular speeds (of rotation). Moreover, the subject is subjected to less anatomical strain or stress because his or her center of mass (usually somewhere in the area of the belt buckle) is substantially aligned with the orthogonal rotational axes. Those of skill in the art also will appreciate that such centered but versatile orthogonal-axes rotation and acceleration of apparatus 10 requires less robust power and drive electro-mechanics and less robust rotational containment and securement, as by axles or spindles and bearings, at either load-bearing end of the orthogonal rotational axes because there is lower linear acceleration, i.e. less angular momentum (moment of inertia), to overcome. This makes possible a higher-performance structure characterized nevertheless by lower power, complexity, weight and cost.

Associated with first axis $A_1$ is a first drive mechanism 22 for imparting controlled rotation to truss frame 14. Associated with second axis $A_2$ is a second drive mechanism 24 for imparting controlled rotation to second frame 18. The drive mechanisms can be operated independently, e.g. to impart rotation to truss frame 14 or oval frame 18 only, or concurrently, e.g. to impart rotation to truss frame 14 and oval frame 18 together.

Apparatus 10 is extremely versatile in its provision of controlled rotation about its two orthogonal rotational axes $A_1$ and $A_2$ (these rotations being indicated in FIG. 1 by single-ended, curved arrows). It can be operated at relatively low angular speeds of tens of degrees/second about axis $A_1$ and/or axis $A_2$, e.g. for medical testing and treatment. Or it may be used at much higher angular speeds of hundreds of degrees/second about either or both axes. Indeed, extremely low angular speeds as low as 1-10°/second (barely more than one rotation per minute to coax an otolith down an ear's semicircular canal) and high angular speeds as high as 3600°/second (up to ten rotations per second to simulate a professional ice skater's closed-spin grand finale) for one or both orthogonal axes are contemplated as being within the spirit and scope of the invention. As will be seen, rotational and angular speed control and resulting orientation of the subject can be scripted in software or commanded by an attendant by use, for example, of a joystick or other easy-to-operate input device such as a push-button control panel.

In accordance with one embodiment of the invention, first and second drive mechanisms 22 and 24 include electric motors 26 and 28 and chain/sprocket drives 30 and 32. Preferably, electric motors 26 and 28 are each powered by pulse-width-modulated (PWM) drive electronics, as are known in the art. PWM control of a motor is a way to deliver variable power to the motor so that the motor can move at varying speeds. The frequency of the so-called 'chopping' of this signal conventionally is between 500 and 1000 Hz. This is in the audible range of hearing and produces an audible and irritating whine. Most preferably, and unlike the prior art, the PWM drive electronics in accordance with the invention is characterized by a fundamental operating frequency, e.g. 19 kHz, that is substantially outside an audible hearing range for a human subject. This unique drive electronics feature greatly benefits human subjects who, perhaps due to a vestibular or other ear semicircular canal disorder, are particularly sensitive to audible noise that is an artifact of conventional PWM motor drive electronics. This invented feature greatly reduces the acoustic burden on both the human subject and the attendant, especially in a small, enclosed diagnostic testing room, by eliminating any audible artifact of the PWM drive technique. Moreover, it reduces noise pollution and thus is more environmentally friendly than prior art PWM motor drive mechanisms.

Those of skill in the art will appreciate that apparatus 10 thus is suitable for controlled orientation of a mammalian, e.g. human, subject for a variety of purposes that are illustrative as described herein and not limiting of the scope of the invention. For example, rotational-chair patient testing is facilitated by the invention, whether it be overall vestibular assessment of a patient including but not limited to motion sickness, vertigo or other inner ear dysfunction, cardiac or blood pressure response to orientational changes, even the most basic audiology assessments. Treatment also is contemplated by use of the novel apparatus, including but not limited to gallstone or kidney stone residual particle removal following surgical, chemical or wave bombardment therapy. Flight simulation or training, pilot training or other educational or gaming applications are also contemplated as being illustrative but not limiting applications. Similarly, rotational-chair subject rotational and/or vibrational stimulus/response of a subject to positive or negative G-forces (whether earth-gravitational or simply accelerational, rotational (e.g. pitch or roll), vibrational), etc. is also facilitated by the invention. These applications are illustrative only and are not intended to limit the invented apparatus and system in any way.

FIG. 1 also illustrates a the three-point load bearing support of truss frame 14 on base 12 defined by a central hub 34 and a laterally spaced pair of wheels $W_L$ and $W_R$. It will be appreciated that these three load-bearing points generally define a triangle and provide an extremely stable rotational foundation for truss frame 14. Those of skill in the art will appreciate that, in accordance with one embodiment of the invention, wheels $W_L$ and $W_R$ are arcuately spaced apart around semicircular rim-support brace member 20 and preferably subtend an acute angle, e.g. less than approximately 90° and preferably less than approximately 45° and most preferably approximately 20-30°, as perhaps best seen in FIG. 4. No other support mechanism and no capture mechanism whatsoever is required in accordance with the invention to provide stable rotational support for rim 16 of truss frame 14. And while semicircular rim-support brace member 20 could extend substantially circularly and concentrically around rim 16, such is neither required nor justified from a cost-benefit standpoint.

It may be seen from FIG. 1 that hub 34 in accordance with another novel aspect of the invention is mounted for rotation on base 12 via a floating plate 40 (refer also to FIG. 5) that mounts truss frame 14 for rotation relative to base 12 in a relatively fixed position. Fixed position is relative because of the unique feature of the floating plate by which a laterally (horizontally) elongated or slotted hole is provided that confines the hub's axle at a fixed elevation thus preventing elevational movement during rotation while intentionally and effectively permitting limited lateral movement (~1½"). This feature accommodates slight vibrational artifacts of less-than-perfect tracking of rim 16 on rim-support brace member 20. Such vibrational artifacts can result from slightly out-of-roundness of rim 16 or of semicircular brace member 20 that results from accumulated manufacturing tolerances or deformations. Remarkably, the floating plate is tolerant of such wiggles and movements as might otherwise derail the rotating truss frame and cause it to roll off the wheels (derailment or so-called 'runout') and fall or tip over. Moreover, were the rotating truss frame to 'run out' of the wheels, the hub axle would prevent the truss frame from moving away from the base 12 and would prevent the truss frame from tilting over.

The remaining structural details of apparatus 10 will be described in more detail below by reference to FIGS. 2, 3, 4, 5, 6 and 7A and 7B.

Figure 2:
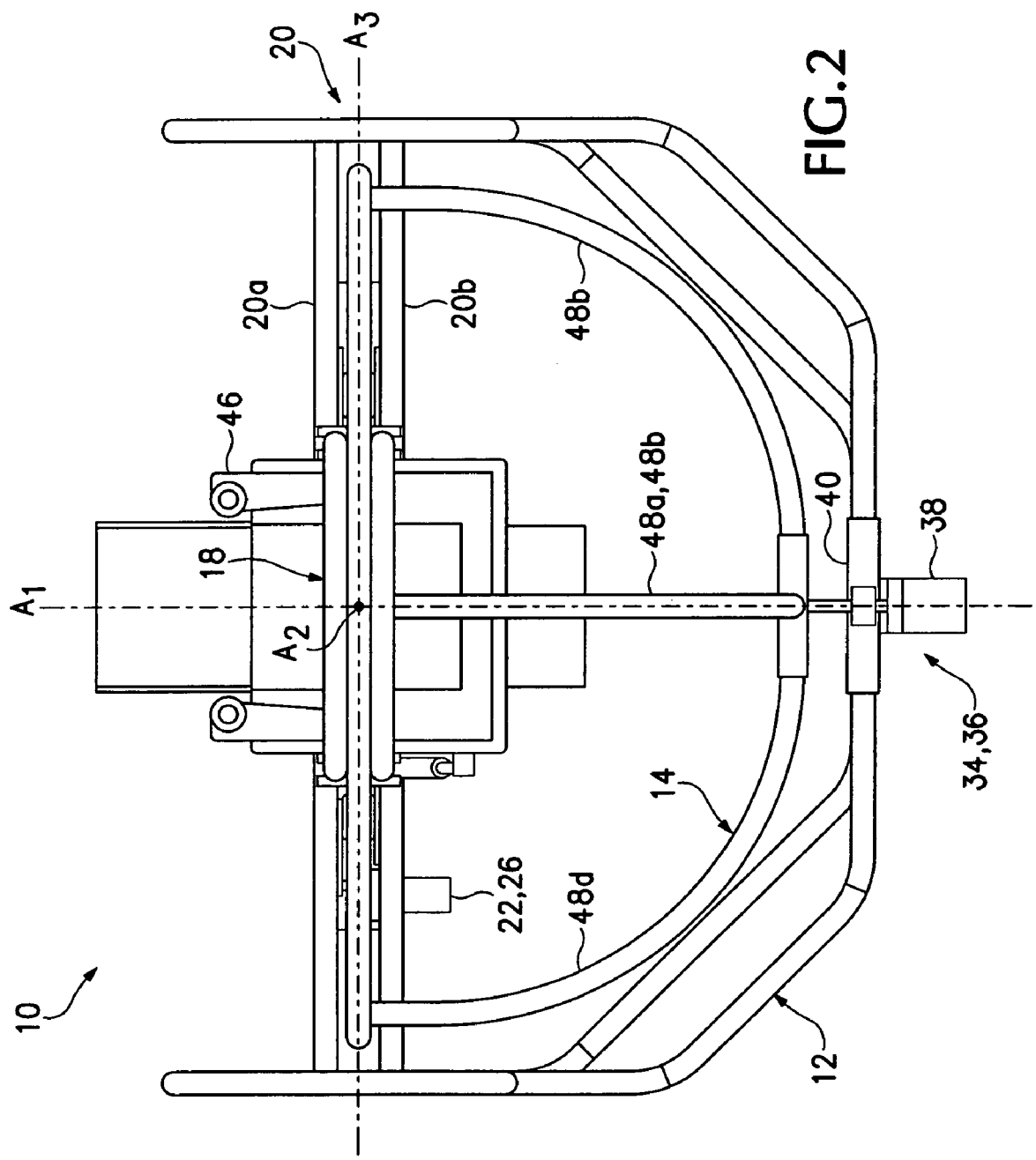
FIG. 2 is a top plan view of the apparatus of FIG. 1.

FIG. 2 illustrates apparatus 10 in a top plan view. It will be appreciated from FIG. 2 that apparatus 10 features a generally semicircular footprint on the floor or ground that supports it. In fact, base 12 can be seen to extend generally semicircularly around truss frame 14, whereby base 12 and frame truss 14 define generally concentric semicircular footprints when apparatus 10 is viewed from above. This is an additional advantage of the invention, in that the configuration of apparatus 10 creates a smaller footprint that fits rather well into a right triangular corner of a room and thus saves space while still affording good access to the subject.

Figure 3:
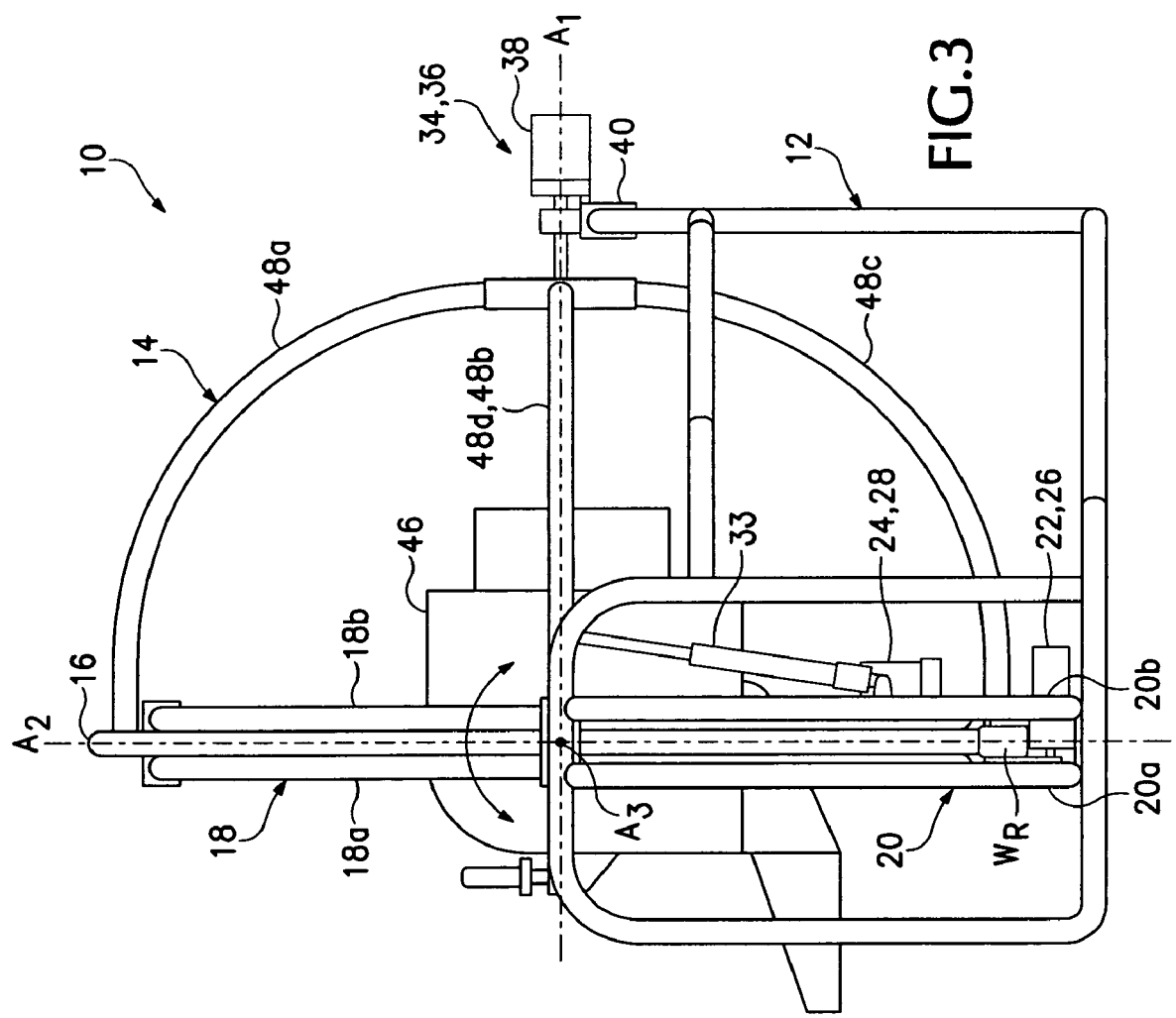
FIG. 3 is a right side elevation of the apparatus of FIG. 1.

FIG. 3 illustrates apparatus 10 in a right side view. FIG. 3 perhaps best illustrates the important hemispheroidal shape of truss frame 14 that, in side elevation, generally describes a semicircle. It can be appreciated from FIG. 3 why the hemispheroidal truss frame 14 is described herein as being asymmetric, since conventional apparatus would have a circular projection in such a side view instead of the semicircular projection of FIG. 3. FIG. 3 also perhaps best illustrates the earth-vertical plane described by rim 16 and the circular opening defined therein. Finally, FIG. 3 perhaps best illustrates the rotation of second frame 18 off-axis (typically a forward tilt of the subject) to align a desired inner ear semicircular canal with a given reference plane preferably using a linear actuator 33 and a local or remote control device (not shown). The desired tilting of the subject, which those of skill in the art will appreciate, is typically achieved by rotating the subject slightly and then fixing the subject in a desired orientation, is indicated in FIG. 3 by a double-ended, curved arrow.

FIG. 3 also shows a first hub 34 extending rearwardly from base 12. It will be appreciated that in accordance with the invention, first hub 34 preferably includes a first slip ring 36 and a first positional encoder 38. First slip ring 36 located on the hub's axle provides one or more commutating circuit connections or channels between fixed base 12 and rotating truss frame 14. Those of skill in the art will appreciate that the slip ring's rotating inner armature is fixed to a hollow shaft that acts as a conduit for signal or power wire harnesses corresponding to the rotating truss frame, while the slip ring's brushes transfer the signal or power to the stationary side corresponding to the fixed base. Those of skill in the art also will appreciate that first absolute positional encoder 38 detects and conveys to drive mechanism 22 or to a remote PC or control device absolute angular position data corresponding with rotation of truss frame 14 about first axis $A_1$. Alternatively, axis $A_1$ positional data could be obtained from an incremental encoder associated with drive mechanism 22 (within the motor itself) but such is less desirable since such would be subject to error from slippage between the rim and the drive roller (wheel).

Figure 4:
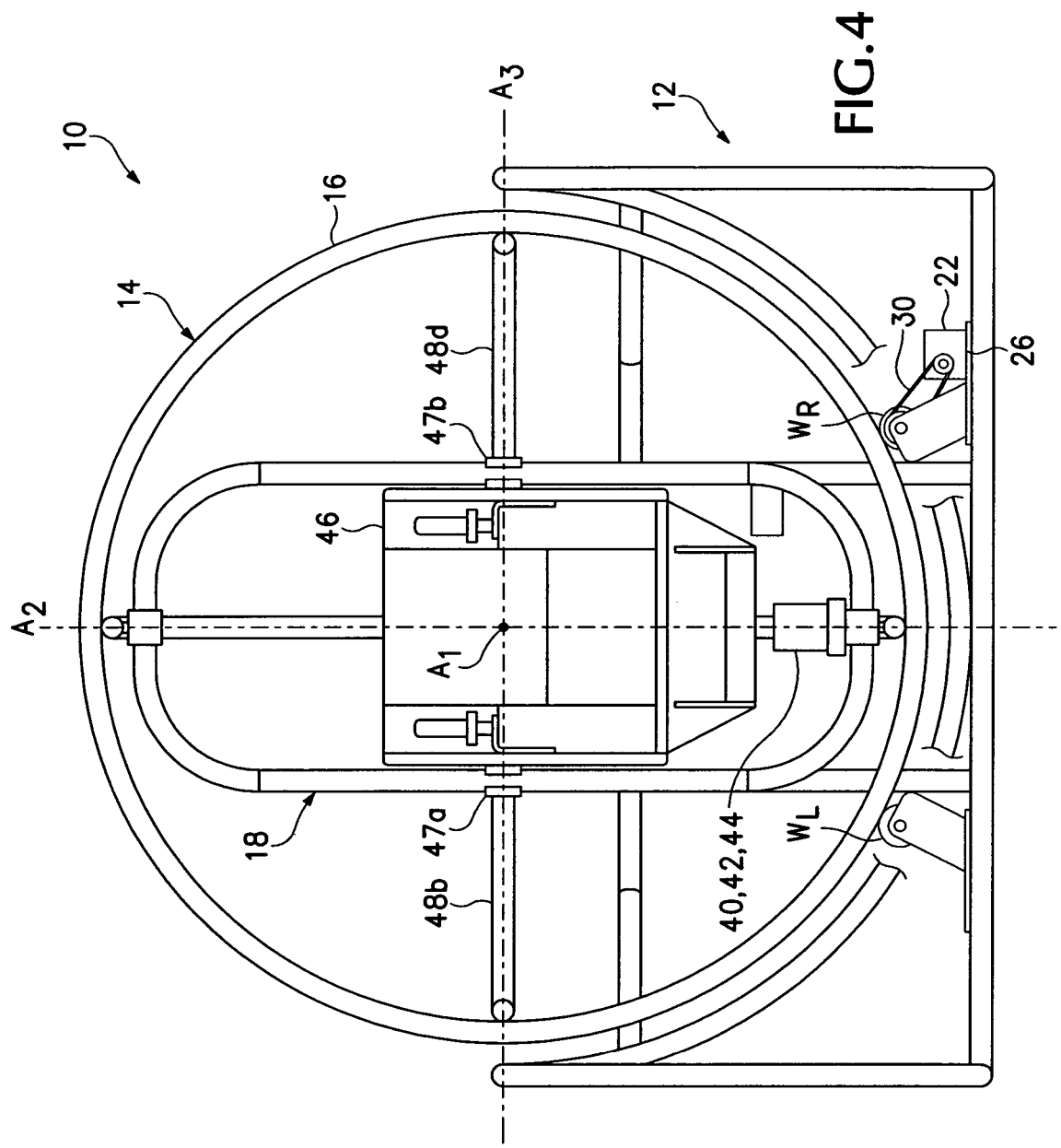
FIG. 4 is a front elevation of the apparatus of FIG. 1.

FIG. 4 illustrates apparatus 10 in front elevation. FIG. 4 perhaps best illustrates the important hemispheroidal shape of truss frame 14 that, in front elevation, generally describes a circle. Apparatus 10 includes a second hub 40 associated with oval second frame 18 that operates similarly to that of first hub 34 described above and includes a second slip ring 42 that also operates similarly to that of first slip ring 36. Those of skill in the art will appreciate that second hub 40 also can have a second, absolute positional encoder 44 therein, since angular rotation data for rotation about axis $A_2$ is absolute (there being no slippage) so that accurate positional data for this second hub can be obtained directly from second positional encoder 44 associated with second drive mechanism 24 (within the motor itself).

In accordance with one embodiment of the invention, motors 26 and 28 that form a part of first and second drive mechanisms 22 and 24 are 180 volt direct current (VDC) permanent brush magnet motors having characteristic high-torque ratings operated at suitable speeds and geared down appropriately via gear mechanisms of any suitable ratios (e.g. between approximately 20:1 and 30:1) including chain/sprocket drives 30 and 32 for desired rotational operating speeds. Those of skill in the art will appreciate that any suitable drive mechanisms are contemplated as being within the spirit and scope of the invention.

First and second slip rings 36 and 42 within the spirit and scope of the invention can be identical with one another. Importantly, they permit the routing of power and AC or DC command and status data respectively to and from the incrementally concentric inner workings of apparatus 10 from the outside world, e.g. a PC-connected umbilical cord. For example, AC power can be conveyed along a wiring harness or cord to the transformers of drive mechanisms 22 and 24 located between the truss frame and the second frame across one channel of slip ring 42 and via the conduits defined within the hollow tubular members (e.g. the hollow axle, struts and rim of truss frame 14). Similarly, DC (e.g. digital) command signals can be conveyed therethrough to control the drive mechanisms. Audio or video signals can be conveyed along a wiring harness to a headphone or video projector within the second frame via the conduits defined within the hollow tubular members thereof (e.g. the hollow axle and rim of second frame 18). (Alternatively, audio or video or other signals can be conveyed wirelessly, via radio frequency (RF) or infrared (IR) transmission.) Similarly, but in the reverse direction, positional encoder data can be conveyed along a wiring harness from either positional encoder to the PC.

Those of skill will appreciate that more or fewer than six channels for conveyance of power and signal can be provided for either or both of slip rings 36 and 42, as various applications may require. It will also be appreciated that one or more given channels can be time-multiplexed to multiply their functionality. It will also be appreciated that one or more channels can be bi-directional, so that in a given application the PC sends commands to the apparatus and in another application the apparatus sends status data to the PC utilizing one or more of the plural slip rings' channels. Any suitable techniques for expanding (or contracting) the number or utility of the slip rings' channels to achieve more (or less) functionality are contemplated as being within the spirit and scope of the invention.

Moreover, those of skill in the art will appreciate that the slip rings provide rotation-orientation-independent power and signal conveyance from a fixed-position PC or remote control device to 3D (two-axis), 360° rotationally dynamic, orientational apparatus 10. Thus, unlimited freedom of 3D rotation is possible while power and signals are conveyed to/from apparatus 10 because the slip rings provide continuous rotational conduction via pairs of rotors and corresponding brushes. In other words, instead of alternating rotation (in what might be viewed as a winding and then a necessary unwinding of a power/signal harness), in accordance with the invention unlimited and continuous uni- or bi-directional rotations are possible because separate wire harnesses are provided within conduits within the rotating members, the wire harnesses being electrically connected to an external umbilical cord via the commutation circuit connections provided by slip rings 36 and 42.

In some testing of patients suspected of having vestibular or other disorders, a hooded patient may be intentionally tilted or rotated off-vertical axis and asked to 'right' (correct or render vertical) his or her orientation or to estimate the direction and extent of the tilt. Alternatively, the patient may be intentionally oriented on-vertical axis and asked to describe the balance sensation (or, more likely, the lack of balance) to the attendant or physician. In such diagnostic cases, apparatus 10 can be used in conjunction with two joysticks or other rotational control input devices: one for the attendant or physician and the other for the patient. Thus, attendant and patient would exercise dual control over the rotational drive mechanisms of apparatus 10, requiring a potential doubling of the command/status signal lines conveyed between the apparatus and a PC. Or the patient might use a microphone and headphone to listen to and answer voiced instructions or questions from the attendant or physician, thus requiring more audio command/status signal lines.

In other testing of patients, the attendant or physician positions a patient in a desired orientation and then observes the patient's nystagmic response to the orientation. This application reinforces the importance of the shape of the hemispheroidal truss of the invention, because it requires close-in or proximate subject observation by an attendant who is typically standing outside the periphery of the apparatus typically near the center of the circular planar opening defined by the truss frame's rim. While nystagmic response can be normal, it also can be abnormal and an indicator of vestibular disorder or other inner ear semicircular canal anomalies. A motion picture camera might be mounted within second frame 18 to record such a nystagmic response, in order to document the attendant's or physician's observations, and such might require another signal to be fed over the command/status signal lines to the PC for recording/archival purposes.

Other accessories can be provided within truss frame 14 or second frame 18. For example, it is sometimes needed for audiologists or physicians to treat patients having hearing disorders or other inner ear problems with vibrational stimuli that impacts directly on the patient's head. Thus, in accordance with the invention, a vibration helmet or other headgear can be provided within second frame 18 that is turned on and off by command from the PC or remote control device via a signal conductor utilizing the slip rings. Myriad other accessories are contemplated as being accommodated by the invention, whether they be command-intensive thus requiring plural in-bound command lines within the umbilical cord, slip ring(s) and wiring harness(es) or plural out-bound status indicator lines within the umbilical cord, slip ring(s) and wiring harness(es) or a combination of the two. All are within the spirit and scope of the invention, whether geared toward medical, educational, entertainment or other applications of versatile apparatus 10.

FIG. 4 illustrates the preferred arcuate spacing of wheels $W_L$ and $W_R$ to subtend an acute angle. It is believed that such an acute angle provides maximum rotational stability to truss frame 14 upon base 12. Those of skill in the art will appreciate that truss frame 14 alternatively could be driven by first drive mechanism 22 located at first hub 34, but that it is preferred to drive truss frame 14 for rotation using a first drive mechanism 22 connected to one or more of wheels $W_L$ and $W_R$. Preferably, wheels $W_L$ and $W_R$ are ball-bearing mounted for rotation and are made of 70 A black polyurethane or similarly durable and resilient material.

In this embodiment of the invention, first hub 34 becomes a passive rather than drive rotational element of apparatus 10 and preferably one or alternatively both of wheels $W_L$ and $W_R$ become the driving force. This provides a safety factor in the case of power failure while apparatus 10 is in operation with a subject therein which may be inverted in second frame 18. If needed, truss frame 14 can be manually rotated to orient the chair and the subject therein upright because slippage is allowed at the frictional interface between the confronting rim and drive or idler wheel. Thus a subject can safely exit apparatus 10 without further incident. Nevertheless, any suitable location for first drive mechanism 22 within apparatus 10 is contemplated as being within the spirit and scope of the invention.

Importantly, as can be seen from FIG. 4, truss frame 14 and second frame 18, as well as portions of base 12, can be easily disassembled, transported and reassembled in situ because they are preferably made of hollow aluminum tubes of circular cross section that are segmented (such segments are delineated in the drawings by short line segments that extend transverse to the axes of the hollow tubular members). It can also be seen from FIG. 4 that a subject-support mechanism or chair 46 is provided within second frame 18 for a seated and suitable secured subject. Those of skill in the art will appreciate that, by virtue of the hollow tubing from which the truss frame and second frame are made, power and signals can be conveyed to chair 46 to power and control a variety of accessories.

In accordance with one embodiment of the invention, the hollow-tube framing members for at least the truss frame and the second frame are made by computerized numerically controlled (CNC) bending of schedule 40 or schedule 80 aluminum tubing around a mandrel. The hollow-tube framing members can be segmented and assembled by use of interior hollow aluminum or steel connectors suitably and durably fastening the segments together, as indicated by segment lines that extend transverse to the long axes of the curved and angled tubular members in the drawings. Those of skill in the art will appreciate that, in accordance with one embodiment of the invention, rim-support brace member 20 includes dual spaced apart members 20a and 20b fore and aft of axis $A_2$ for added structural integrity. Similarly, for increased structural integrity, second frame 18 also includes dual spaced apart members 18a and 18b fore and aft of axis $A_2$. Preferably, the latter are fastened together in the middle of the long axis of oval frame 18 with a pair of laterally spaced, machining-formed aluminum devises 47a, 47b and suitably durable fastening hardware.

In order to assemble hemispheroidal truss frame 14 with a true circular and planar configuration of rim 16, and with a true hemispherical configuration overall, a jig (not shown) can be used to assemble the four rim segments on a planar work surface with three or more and preferably four struts 48a, 48b, 48c, 48d evenly arcuately spaced around the circumference of the circular rim and connected to first hub 34 at the non-concentric center of the circular rim as defined by axis $A_1$ aligned to extend through the true center of first hub 34 and through the true center of the circle described by rim 16. Any suitable assembly steps or tools or are contemplated, however, as being within the spirit and scope of the invention.

Figure 5:
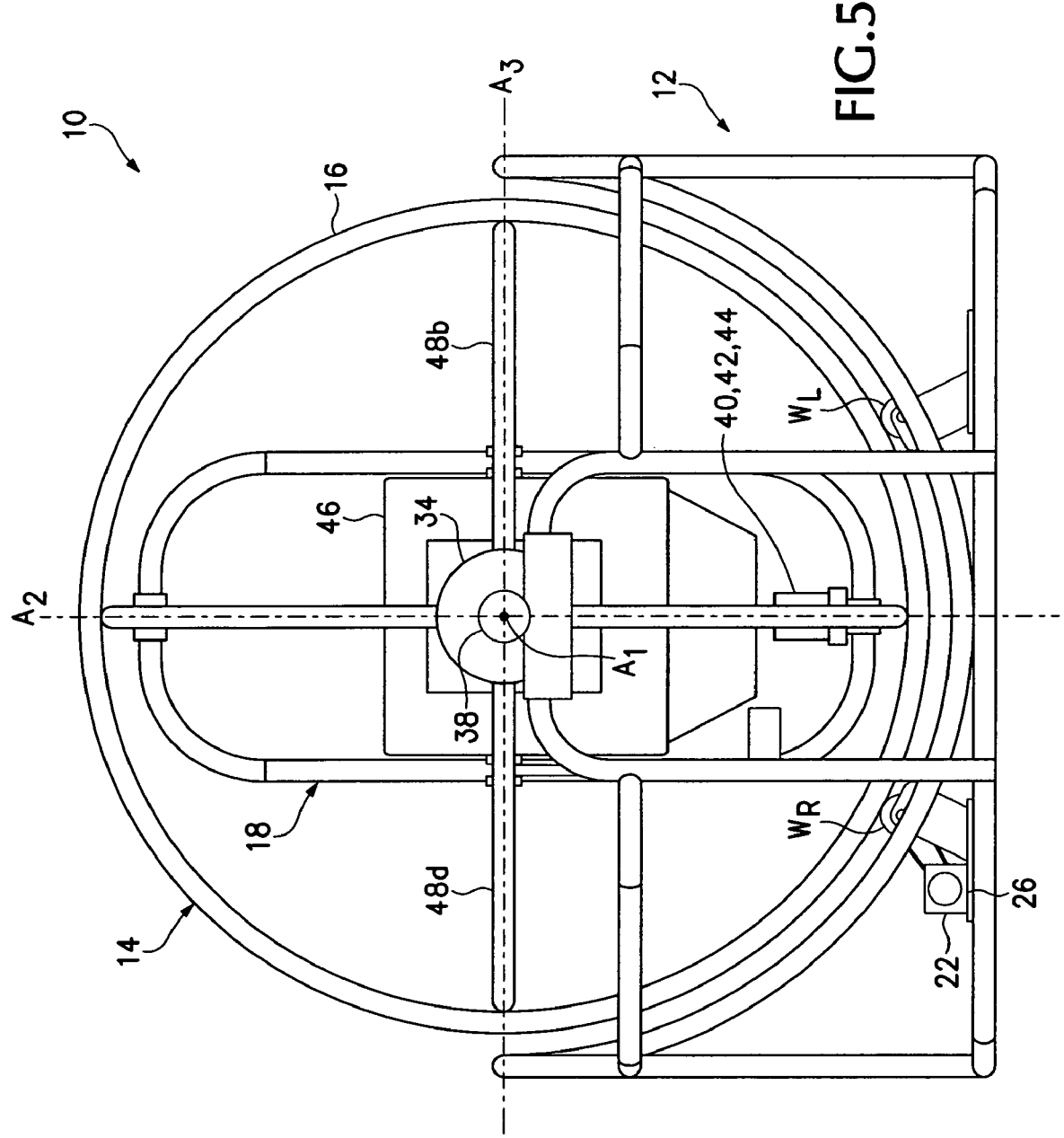
FIG. 5 is a rear elevation of the apparatus of FIG. 1.

FIG. 5 illustrates apparatus 10 in rear elevation, and perhaps best illustrates floating plate 40 that rotatably mounts truss frame 14 to base 12 via a slotted hole to accommodate slight side-to-side movement while restraining up-and-down movement of the rotating truss frame 14 relative to base 12.

Figure 6:
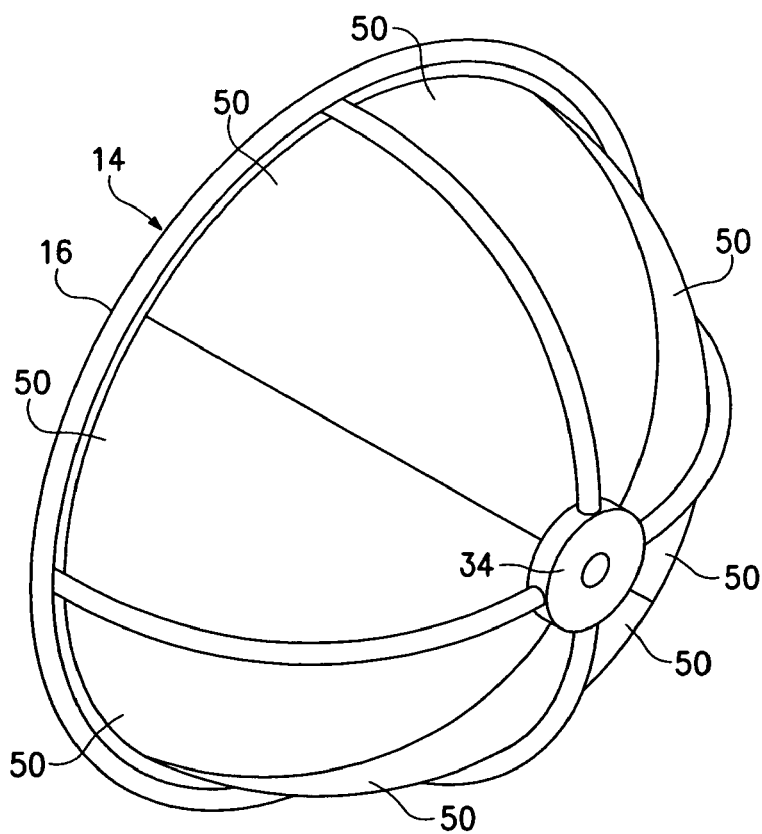
FIG. 6 is a rear isometric view of the apparatus of FIG. 1 with an opaque hemispheroidal screen therein.

Visible-spectrum or infrared goggles or headphones or video projectors or cameras or joysticks or personal digital assistants or laptop computers can be mounted or otherwise provided adjacent chair 46 for various applications. FIG. 6 shows a particular application for apparatus 10 by which an opaque hemispheroidal screen 50 (shown in substantially identical pie-slice-shaped pieces in FIG. 6 for clarity) can be affixed either in a unit or in segments to the inside of truss frame 14, preferably with each segment's edge overlapping the next to reduce light permeability at the seams. Screen 50 can be used to obscure the subject's vision, e.g. restricting light from reaching the eyes of a subject facing the screen, or can be used to project still or moving images for viewing by the subject. These and other suitable uses for a screen 50 are contemplated as being within the spirit and scope of the invention.

Those of skill also will appreciate that apparatus 10 can form a part of a larger system including, for example, a personal computer (PC) or workstation running diagnostic and control software. Typically, it will be understood that the drive electronics (which may include a microcomputer or microprocessor and associated memory and logic and signal conditioning devices) described above primarily control the motors and thus the rotation of the frame truss and second frame. Thus, outboard commands can be routed to apparatus 10 by use of an umbilical cord that permits a suitably programmed PC to control the apparatus in accordance with a defined orientational script that implements desired diagnostic or therapeutic steps. Alternatively, the subject or an attendee can control the subject's orientation and thus his or her diagnostic or therapeutic steps by use of a joystick or other input control device to which the PC is programmed to respond by sending drive commands to the apparatus's drive electronics via the umbilical cord. Any suitable system architecture—whereby control sequences are stored in memory or commanded from within the apparatus or from outside the apparatus—is contemplated as being within the spirit and scope of the invention. Thus, subject testing and treatment utilizing the invented apparatus can be as automatic as desired on the one hand or as manual as desired on the other.

Figures 7A, 7B:
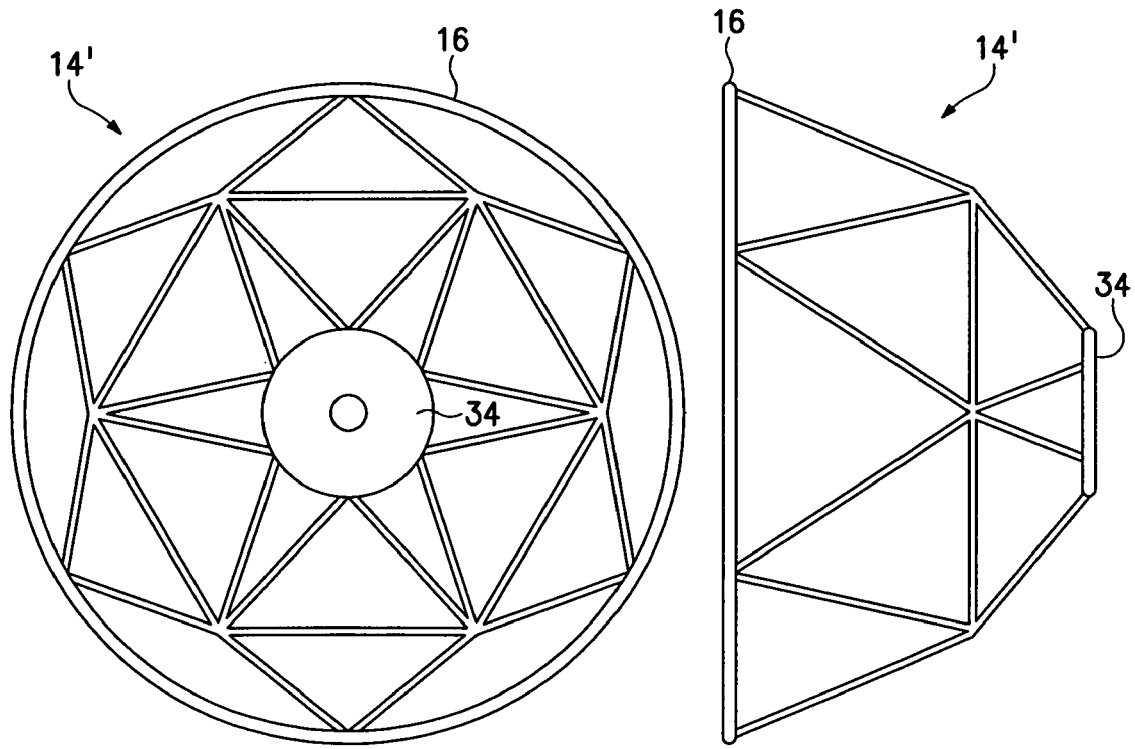
FIGS. 7A and 7B illustrate only the hemispheroidal truss frame portion of an alternative embodiment of the invented apparatus in front and right-side elevations, respectively.

FIGS. 7A and 7B illustrate only a hemispheroidal truss frame 14' of an alternative embodiment of the invented apparatus in front and right-side elevations, respectively. FIGS. 7A and 7B illustrate that, instead of the three or more struts being arcuate (e.g. the four arcuate struts 48a, 48b, 48c and 48d described above) to define the outer curve of the hemispheroidal truss frame, a geodesic dome configuration of struts is possible. Thus, truss frame 14' generally describes a hemisphere in shape, but three or more angular, piece-wise linear struts connect first hub 34 to rim 16 in a network of triangular segments that provide the required structural integrity to truss frame 14'. Those of skill in the art will appreciate that alternative geodesic dome-type configurations are possible, having more or fewer such triangular segments of different angles and 'surface' areas, for example, within the spirit and scope of the invention.

Those of skill in the art will appreciate that there are suitable alternatives to the embodiments described and illustrated herein in which an optional screen is affixed to a curvilinear or piece-wise curvilinear spidery truss frame strut array, within the spirit and scope of the invention. Apparatus 10 can be rendered more solid than spidery, with a contiguous, and thus substantially opaque, concave hemispheroidal dish-shaped truss frame 14. "Shell", as used herein, broadly connotes and embraces any such hemispheroidal structure whether configured as an open "cage-like truss or a solid dish. (It will be appreciated that a solid dish-like shell obviates the screen requirement.) Such a solid or closed structure can be made of a lightweight material, e.g. fiberglass, polystyrene foam, graphite or another durable, shape-retentive, structural robust material, in accordance with the spirit and scope of the invention.

Those of skill in the art will appreciate that, in order to impart to the mammalian subject translational, e.g. elevational or vibrational, or other movement or stimuli, apparatus 10 can be augmented in desirable ways. For example, a linear actuator can interpose chair 46 and oval frame 18, the linear actuator translating the chair relative to the oval frame in a desirable elevational transportational (e.g. height adjustment) or oscillatory manner to impart elevational movement or vibration to the subject generally along an axis within the circular opening defined by rim 16 and extending parallel to the oval frame's long axis.

Alternatively or additionally, a linear actuator can interpose apparatus 10 and the ground or floor that supports it, the linear actuator translating the movable apparatus relative to the ground or floor in a desirable laterally translational or oscillatory manner to impart lateral movement or vibration to the subject generally along an axis within circular opening defined by rim 16 and extending parallel laterally therethrough to impart side-to-side translational or vibratory motion to the subject. Such can be accomplished by mounting translatable apparatus 10 on a static, ground- or floor-fixed linear track, with the side-to-side linear actuator interposing the two.

Finally, within the spirit and scope of the invention, a rotary actuator in the form of a large turntable can be provided between apparatus 10 and the ground or floor that supports it, the rotary actuator imparting rotation or even revolution to apparatus 10 in addition to the integral rotations provided by apparatus 10. Such would, for example, simulate yaw and/or banking in aerobatic or car-racing maneuvers and would add to the realism of such environmental simulation or gaming. The umbilical cord and the novel combination of hollow tubing, wiring harnesses and two or more slip rings for continuous rotational conduction and conveyance of power and/or command/status signals would enable a subject to control this ground-relative rotary aspect of the subject's orientation, along with the 3D 360° about the two principal orthogonal axes $A_1$ and $A_2$, via a joystick held and operated by the subject within the second oval frame.

If oscillation is desired from either linear actuator or the rotary actuator described above, it is believed that either or both can be operated at up to approximately 10 Hz and preferably up to only approximately 2-3 Hz to simulate environmental turbulence by oscillation. But within the spirit and scope of the invention, any suitable frequency of oscillation or speed of translation imparted by the linear actuators is contemplated as being within the spirit and scope of the invention.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

From the foregoing, those of skill in the art will appreciate that several advantages of the present invention include the following.

The present invention provides all of the many advantages described and illustrated above and summarized below.

The apparatus and system provide a stable, lightweight but durable 3D, 360° rotation of a mammalian subject for controlled subject orientation. They do so in the form of an inexpensive hemispheroidal truss spatial manipulator that is motor driven for rotation of the subject in at least two orthogonal axes and for pivotal adjustment of the subject in a third axis orthogonal to the other two. Vestibular or other physiological disorders can be diagnosed and optionally treated by an attendant such as a physician who manually or programmatically commands orientation, for example, of the subject's inner ear semicircular (or other) canal for otolith (or other particulate) repositioning under the force of gravity, or under the force of angular acceleration. Other subject physiological traits that are impacted by subject orientation can be assessed including cardiac and blood pressure anomalies that may or may not be relatable to vestibular or other observable disorders. Yet the apparatus is small in footprint, fits easily in corners of smaller rooms and breaks down (disassembles) easily for transportation.

It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. Spatial manipulator apparatus for a mammalian subject comprising:
   a stabilizing base;
   a hemispheroidal truss frame mounted for rotation on the stabilizing base, the truss frame supporting and stabilizing an outer generally circular rim in relation to a hub located at its rotational axis; and
   a second frame mounted orthogonally within the outer rim on a second rotational axis, the second frame being configured to support a mammalian subject during spatial manipulation thereof by rotation about one or more of the orthogonal rotational axes.

2. The apparatus of claim 1, wherein the truss frame and the second frame are driven for rotation about the orthogonal rotational axes to achieve a desired mammalian-subject spatial orientation.

3. The apparatus of claim 1 which further comprises:
   a chair-like structure mounted within the second frame for rotation about a third axis that is substantially orthogonal to the first and second orthogonal rotational axes, wherein the third axis provides for rotational pivotal alignment of the chair-like structure relative to the second frame.

4. The apparatus of claim 1, wherein the truss frame includes:
   a substantially circular rim member mounting the second frame for rotation therein,
   three or more struts connecting from circumferential substantially evenly spaced locations along the circular rim member to a point of convergence on the truss frame through which the first axis extends; and
   the hub at the point of convergence mounting the three or more struts.

5. The apparatus of claim 4, wherein the three or more struts are configured generally as a geodesic dome.

6. The apparatus of claim 4, wherein the base includes a semi-circular support member mounting two wheels, the two wheels supporting the rim member for rotation about the first axis, and wherein the base further includes a brace bearing the hub for rotation thereof about the first axis.

7. The apparatus of claim 5, wherein the hub and the two wheels provide a three-point support for the truss frame mounted for rotation on the base and for the second frame mounted for rotation therein, at least one of the hub and the two wheels being driven for rotation of the truss frame about the first axis and at least another of the hub and the two wheels being idle.

8. The apparatus of claim 4, wherein the second frame is mounted for rotation relative to the truss frame on two opposing bearings, and wherein the rim member and the three or more struts are hollow tubular structures, and wherein the hollow tubular structures and the bearings form conduits configured to convey electrical and power wire harnesses therethrough.

9. The apparatus of claim 8, wherein at least one of the hub and the two bearings includes a slip ring.

10. The apparatus of claim 4, wherein the hub is mounted to a spindle for rotation relative to the base via a floating plate assembly that fixes vertical positioning of the hub relative to the base but permits controlled horizontal translation of the hub relative to the base, during rotation of the truss frame.

11. The apparatus of claim 1 which further comprises:
an opaque hemispheroidal screen extending substantially around but within the truss frame, the screen configured as a barrier to ambient light transmission to the interior of the truss frame and being configured further for still or moving picture video projection thereon.

12. The apparatus of claim 1, wherein the second frame is generally oval and extends circumferentially around the mammalian subject supported thereby, the second frame including dual spaced hollow tubular oval rims.

13. The apparatus of claim 1, wherein the second frame generally extends circumferentially around the mammalian subject supported thereby, the second frame including dual spaced hollow tubular oval rims.

14. The apparatus of claim 1 which further comprises:
a first rotational encoder operatively connected with the truss frame; and
a second rotational encoder operatively connected with the second frame,
the first and second rotational encoders sensing the rotational orientations of the truss frame and of the second frame about the first and second axes.

15. The apparatus of claim 1, which further comprises:
a chair for the mammalian subject, the chair mounted within the second frame; and
a linear actuator between the chair and the second frame for linear translation of the chair relative to the second frame along an axis that is substantially parallel to a long axis of the second frame.

16. The apparatus of claim 1, which further comprises:
a linear track equipped with a linear actuator for linear translation of the base mounting the truss frame and the second frame along an axis that is substantially perpendicular to the first axis.

17. Mammalian-subject spatial manipulator apparatus comprising:

a fixed base having an upright hub-support portion in a first region of the base and having an upright rim-support portion in a second region of the base opposite the first region; and
a generally hemispheroidal truss frame mounted on an upright portion of the base, the frame including a hub defining a first axis of rotation, three or more struts mounted thereto and extending arcuately to three or more circumferentially substantially evenly spaced mounting positions on a substantially circular rim, the truss frame being rotatable through 360° about the first axis, the truss frame further including a second frame for supporting a mammalian subject, the second frame being mounted along a diameter of the circular rim for 360° rotation in a second axis of rotation that is substantially perpendicular to the first axis of rotation,
the rim-support portion of the base mounting at least two 360° rotatable wheels each having a concave channel conforming to the outer surface of the circular rim, whereby the at least two wheels and the hub provide three-point load-bearing and rotational support for the truss frame.

18. The apparatus of claim 17, wherein the base extends generally semicircularly around the truss frame, whereby the base and the truss frame define generally concentric semicircular footprints when the apparatus is viewed from the top.

19. The apparatus of claim 17, wherein the upright rim-support portion of the base extends only semi-circularly around the substantially circular rim.

20. The apparatus of claim 17, wherein the truss frame extend upwardly from the base to a first height, the upright rim-support portion of the base extends upwardly from the base to a second height that is less than or equal to approximately half the first height.

21. The apparatus of claim 17, wherein the truss frame extends upwardly from the base to a first height, and wherein the upright rim-support portion of the base extends only semi-circularly around the substantially circular rim and extends upwardly from the base to a second height that is less than or equal to approximately half the first height.

22. The apparatus of claim 21, wherein the upright rim-support portion of the base includes two or more rotatable wheels each having a concave channel conforming to the outer surface of the circular rim, the two or more rotatable wheels being generally symmetrically semi-circularly spaced apart along the upright rim-support portion of the base.

23. The apparatus of claim 22, wherein at least one of the two or more rotatable wheels is driven by a drive mechanism to provide for controlled 360° rotation of the truss frame by frictional engagement with the circular rim and at least another of the two or more rotatable wheels is idle.

24. The apparatus of claim 23, wherein the truss frame including the circular rim and the second frame is formed of tubular structures having hollow interiors configured to act as a conduit for an electrical or power harness extending therethrough.

25. The apparatus of claim 24, wherein the hub is mounted to a spindle for rotation relative to the base via a floating plate assembly that fixes vertical positioning of the hub relative to the base but permits controlled horizontal translation of the hub relative to the base, during rotation of the truss frame.

26. A spatial orientation system for a human subject, the system comprising:
a hemispheroidal shell having a central hub defining a first substantially horizontal rotational axis and a substantially circular rim defining a substantially circular planar opening, the first rotational axis extending through the central hub and through a center of the substantially circular planar opening normal thereto;

the shell being mounted for rotation about the first axis on a stabilizing base with the circular planar opening in a vertical orientation; and a mammalian-subject frame mounted for rotation about a second axis substantially perpendicular to the first axis within the circular planar opening of the hemispheric shell, the shell, the base and the support mechanism being configured for controlled orientation of a mammalian subject secured within the frame.

27. The system of claim 26, wherein the base includes a substantially semi-circular upright rim-support brace having two or more wheels rotatably mounted thereon for aligned rotation within the circular planar opening, each of the two or more wheels each having a concave channel conforming to the outer surface of the circular rim, the two or more rotatable wheels being generally symmetrically semi-circularly spaced apart along the upright rim-support brace.

28. The system of claim 27, wherein the shell extends upwardly from the base to a first height, and wherein the upright rim-support brace extends upwardly from the base to a second height that is less than or equal to approximately half the first height.

29. The system of claim 28, wherein the shell, the base and the frame are configured for controlled three-dimensional (3D) 360° orientation of the mammalian subject about the first and second axes.

30. The system of claim 29 which further comprises:

a first drive mechanism mounted on the base and configured to rotate the shell about the first axis; and a second drive mechanism mounted on the shell and configured to rotate the frame about the second axis.

31. The system of claim 30, wherein the first and the second drive mechanisms each include motor powered by pulse-width-modulated (PWM) drive electronics the fundamental operating frequency of which is substantially outside a predefined audible hearing range for a human subject.

32. The system of claim 29, wherein the rim takes the form of a substantially circular rim member that defines the substantially circular planar opening, and wherein the shell includes three or more struts extending from the central hub to substantially evenly spaced locations around the circumference of the rim member, wherein the frame is mounted for rotation relative to the shell on two opposing bearings, wherein the rim member and the three or more struts are hollow tubular structures, and wherein the hollow tubular structures and the bearings form conduits configured to convey electrical signal and power wire harnesses therethrough.

33. The system of claim 29, wherein the shell includes a substantially circular and substantially closed dish-like surface including the substantially circular rim that defines the substantially circular planar opening, the shell extending hemispheroidally from the central hub, wherein the frame is mounted for rotation relative to the shell on two opposing hollow bearings provided in the rim, wherein the shell includes one or more hollow conduits extending from the hub to the rim and wherein the rim includes one or more hollow conduits, and wherein the hollow conduits are configured to convey electrical signal and power wire harnesses therethrough.

* * * * *